(12) United States Patent
Zhou et al.

(10) Patent No.: US 7,082,182 B2
(45) Date of Patent: Jul. 25, 2006

(54) COMPUTED TOMOGRAPHY SYSTEM FOR IMAGING OF HUMAN AND SMALL ANIMAL

(75) Inventors: Otto Z. Zhou, Chapel Hill, NC (US); Jianping Lu, Chapel Hill, NC (US); Yueh Lee, Durham, NC (US); Weili Lin, Chapel Hill, NC (US); Yuan Cheng, Chapel Hill, NC (US); Jian Zhang, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/923,385

(22) Filed: Aug. 20, 2004

(65) Prior Publication Data

US 2006/0008047 A1  Jan. 12, 2006

Related U.S. Application Data

(63) Continuation-in-part of application No. 10/051,183, filed on Jan. 22, 2002, now Pat. No. 6,876,724, which is a continuation-in-part of application No. 09/679,303, filed on Oct. 6, 2000, now Pat. No. 6,553,096, application No. 10/923,385, which is a continuation of application No. 10/421,931, filed on Apr. 24, 2003, now abandoned.

(51) Int. Cl.
*G01N 23/00* (2006.01)
(52) U.S. Cl. .......................... 378/10; 378/122
(58) Field of Classification Search .................... 378/4, 378/122, 15, 208–209, 197, 10, 136, 12
See application file for complete search history.

(56) References Cited

U.S. PATENT DOCUMENTS

| | | | |
|---|---|---|---|
| 3,733,484 A | 5/1973 | Bayard | |
| 3,921,022 A | 11/1975 | Levine | |
| 4,253,221 A | 3/1981 | Cochran, Jr. et al. | |
| 4,289,969 A | 9/1981 | Cooperstein et al. | |
| 4,958,365 A | 9/1990 | Sohval et al. | |
| 5,129,850 A | 7/1992 | Kane et al. | |
| 5,138,237 A | 8/1992 | Kane et al. | |

(Continued)

OTHER PUBLICATIONS

M. D. Bentley et al., "The Use of Microcomputed Tomography to Study Microvasculature in Small Rodents", *Am J Physiol Regulatory Integrative Comp Physiol*, 282, pp. R1267-1279, 2002.

(Continued)

*Primary Examiner*—David V. Bruce
*Assistant Examiner*—Hoon Song
(74) *Attorney, Agent, or Firm*—Jenkins, Wilson, Taylor & Hunt, P.A.

(57) ABSTRACT

Computed tomography device comprising an x-ray source and an x-ray detecting unit. The x-ray source comprises a cathode with a plurality of individually programmable electron emitting units that each emit an electron upon an application of an electric field, an anode target that emits an x-ray upon impact by the emitted electron, and a collimator. Each electron emitting unit includes an electron field emitting material. The electron field emitting material includes a nanostructured material or a plurality of nanotubes or a plurality of nanowires. Computed tomography methods are also provided.

12 Claims, 6 Drawing Sheets

U.S. PATENT DOCUMENTS

| | | | |
|---|---|---|---|
| 5,245,648 A * | 9/1993 | Kinney et al. | 378/43 |
| 5,305,363 A * | 4/1994 | Burke et al. | 378/4 |
| 5,377,249 A | 12/1994 | Wiesent et al. | |
| 5,412,703 A * | 5/1995 | Goodenough et al. | 378/8 |
| 5,424,054 A | 6/1995 | Bethune et al. | |
| 5,616,368 A | 4/1997 | Jin et al. | |
| 5,623,180 A | 4/1997 | Jin et al. | |
| 5,637,950 A | 6/1997 | Jin et al. | |
| 5,648,699 A | 7/1997 | Jin et al. | |
| 5,726,524 A | 3/1998 | Debe | |
| 5,773,834 A | 6/1998 | Yamamoto et al. | |
| 5,773,921 A | 6/1998 | Keesmann et al. | |
| 5,973,444 A | 10/1999 | Xu et al. | |
| RE36,415 E * | 11/1999 | McKenna | 378/4 |
| 5,976,444 A | 11/1999 | Pearson et al. | |
| 6,019,656 A | 2/2000 | Park et al. | |
| 6,057,637 A | 5/2000 | Zettl et al. | |
| 6,087,765 A | 7/2000 | Coll et al. | |
| 6,250,984 B1 | 6/2001 | Jin et al. | |
| 6,259,765 B1 | 7/2001 | Baptist | |
| 6,277,318 B1 | 8/2001 | Bower et al. | |
| 6,280,697 B1 | 8/2001 | Zhou et al. | |
| 6,333,968 B1 * | 12/2001 | Whitlock et al. | 378/136 |
| 6,334,939 B1 | 1/2002 | Zhou et al. | |
| 6,385,292 B1 * | 5/2002 | Dunham et al. | 378/122 |
| 6,440,761 B1 | 8/2002 | Choi | |
| 6,456,691 B1 | 9/2002 | Takahashi et al. | |
| 6,459,767 B1 | 10/2002 | Boyer | |
| 6,553,096 B1 | 4/2003 | Zhou et al. | |
| RE38,223 E | 8/2003 | Keesmann et al. | |
| 6,630,772 B1 | 10/2003 | Bower et al. | |
| 6,650,730 B1 | 11/2003 | Bogatu et al. | |
| 6,674,837 B1 * | 1/2004 | Taskar et al. | 378/122 |
| RE38,561 E * | 8/2004 | Keesmann et al. | 313/309 |
| 6,787,122 B1 | 9/2004 | Zhou | |
| 6,850,595 B1 | 2/2005 | Zhou et al. | |
| 6,876,724 B1 | 4/2005 | Zhou et al. | |
| 2002/0085674 A1 | 7/2002 | Price et al. | |
| 2002/0094064 A1 | 7/2002 | Zhou et al. | |
| 2002/0140336 A1 | 10/2002 | Stoner et al. | |
| 2002/0171357 A1 | 11/2002 | Sun et al. | |
| 2003/0002627 A1 | 1/2003 | Espinosa et al. | |
| 2003/0102222 A1 | 6/2003 | Zhou et al. | |
| 2003/0198318 A1 | 10/2003 | Price et al. | |
| 2004/0036402 A1 | 2/2004 | Keesmann et al. | |
| 2004/0213378 A1 | 10/2004 | Zhou et al. | |

OTHER PUBLICATIONS

L. A. Feldkamp et al., "Practical cone-beam algorithm", *J. Opt. Soc. Am.*, 1(a):612-619, 1984.

J. Hu et al., "Chemistry and Physics in One Dimension: Synthesis and Properties of Nanowire and Nanotubes", *Accounts of Chemical Research*, vol. 32, pp. 435-445, 1999.

O. Zhou et al., "Materials Science of Carbon Nanotubes: Fabrication, Integration, and Properties of Macroscopic Structures of Carbon Nanotubes", *Acc. Chem. Res.*, vol. 35, pp. 1045-1053 (2002).

C. Bower et al., "Fabrication and Field Emission Properties of Carbon Nanotube Cathodes", *Mat. Res. Soc. Symp. Proc.*, vol. 593, pp. 215-220, 2000.

Y. Saito et al., "Field Emission Patterns from Single-Walled Carbon Nanotubes", *Jpn. J. Appl. Phys.*, vol. 36, pp. L1340-L1342, Part 2, No. 10A, Oct. 1, 1997.

Y. Saito et al., Cathode Ray Tube Lighting Elements with Carbon Nanotube Field Emitters, *Jpn. J. Appl. Phys.*, vol. 37, pp. L346-L348, Part 2, No. 3B, Mar. 15, 1998.

W. Zhu et al., "Large Current Density from Carbon Nanotube Field Emitters", *Appl. Phys. Lett.*, American Institute of Physics, vol. 75, No. 6, pp. 873-875, Aug. 9, 1999.

Radiologic Science for Technologist, S. C. Bushong, Mosby Year Book, 1997 (excerpt relating to focusing and thermionic emission).

Zhu et al., "Low Field Electron Emission from Undoped Nanostructured Diamond", *Science*, vol. 282, pp. 1471-1473, Nov. 20, 1998.

Brodie et al., "Vacuum Microelectronics", *Advances in Electronics and Electron Physics*, edited by P.W. Hawkes, vol. 83, pp. 1-106, 1992.

Okano et al., "Electron emission from nitrogen-doped pyramidal-shape diamond and its battery operation", *Appl. Phys. Lett.*, 70 (16), pp. 2201-2203, Apr. 21, 1997.

Okano et al., "Fabrication of a diamond field emitter array", *Appl. Phys. Lett.*, 64 (20), pp. 2742-2744, Mary 16, 1994.

Kumar et al., "Diamond-based field emission flat panel displays", *Solid State Technology*, vol. 38, pp. 71-74, May 1995.

Geis et al., "Diamond emitters fabrication and theory", *J. Vac. Sci. Technol. B*, 14(3), May/Jun. 1996, pp. 2060-2067.

Rinzler et al., "Unraveling Nanotubes: Field Emission from an Atomic Wire", *Science*, vol. 269, pp. 1550-1553, 1995.

de Heer et al., "A Carbon Nanotube Field-Emission Electron Source", *Science*, vol. 270, pp. 1179-1180, Nov. 17, 1995.

Okazaki et al., "A New Emission Spectrum of $Au_2$ in the Gas Evaporation Technique: 761-809 nm", *Jpn. J. Appl. Phys.*, vol. 37, Pt. 1, No. 1, p. 349, (1998).

Wang et al., "Field emission from nanotube bundle emitters at low fields", *Appl. Phys. Lett.* 70(24), pp. 3308-3310, Jun. 16, 1997.

Yagishita et al., "Effects of Cleavage on Local Cross-Sectional Stress Distribution in Trench Isolation Structure", *Jpn. J. Appl. Phys.*, vol. 36, Part 1, No. 3B, pp. 1335-1340, 1997.

Wang et al., "A nanotube-based field-emission flat panel display", *Appl. Phys. Lett.* 72(2), pp. 2912-2913, Jun. 11, 1998.

Bonard et al., "Field emission from single-wall carbon nanotube films", *Appl. Phys. Lett.* 73(7), pp. 918-920, Aug. 17, 1998.

Thess et al., "Crystalline Ropes of Metallic Carbon Nanotubes", *Science* 273, pp. 483-487, Jul. 26, 1996.

Bower et al., "Synthesis and structure of pristine and alkali-metal-intercalated single-walled carbon nanotubes", *Appl. Phys.* A67, pp. 47-52, 1998.

Tang et al., "Electronic Structures of Single-Walled Carbon Nanotubes Determined by NMR", *Science*, vol. 288, pp. 492-494, Apr. 21, 2000.

Journet et al., "Large-scale production of single-walled carbon nanotubes by the electric-arc technique", *Nature*, vol. 388, pp. 756-758, Aug. 21, 1997.

Cassell et al., "Large Scale CVD Synthesis of Single-Walled Carbon Nanotubes", *J. Phys. Chem. B* 103, pp. 6484-6492, Jul. 20, 1999.

U.S. Appl. No. 09/351,537, filed Jul. 1, 1999, Bower et al.

* cited by examiner

COMPUTED TOMOGRAPHY SYSTEM FOR IMAGING OF HUMAN AND SMALL ANIMAL

RELATED APPLICATIONS

This application is a continuation-in-part of U.S. patent application Ser. No. 10/051,183 filed Jan. 22, 2002, now U.S. Pat. No. 6,876,724, which is a continuation-in-part of U.S. patent application Ser. No. 09/679,303 filed Oct. 6, 2000, now U.S. Pat. No. 6,553,096 issued Apr. 22, 2003. This application is also a continuation of U.S. patent application Ser. No. 10/421,931 filed Apr. 24, 2003, now abandoned. The contents of all of the above-cited applications being incorporated here by reference.

STATEMENT REGARDING FEDERALLY SPONSORED RESEARCH OR DEVELOPMENT

At least some aspects of this invention were made with Government support under the sponsorship of the Office of Naval Research, Contract No. N00014-98-1-0597. The Government may have certain rights in this invention.

BACKGROUND

1. Field of the Invention

The present invention relates generally to field emission cathodes for x-ray radiation sources. More particularly, the present invention relates to carbon nanotube field emission cathodes and methods of manufacture and operation of such cathodes in linear or area x-ray radiation sources with individually addressable multi-beam x-rays suitable for use in diagnostic, imaging, and inspection applications.

2. Background of the Invention

In the description of the background of the present invention that follows reference is made to certain structures and methods. Such references should not necessarily be construed as an admission that these structures and methods qualify as prior art under the applicable statutory provisions. Applicants reserve the right to demonstrate that any of the referenced subject matter does not constitute prior art with regard to the present invention.

Computed tomography (CT) technology is widely used for medical, industrial and security imaging purposes. The designs of typical computed tomography machines have gone through major evolutions. For example, for conventional x-ray imaging, a three-dimensional (3-D) object is illuminated to form a two-dimensional (2-D) image. As a result, the spatial resolution in the illumination direction is lost. This limitation can be overcome in computed tomography systems by obtaining projection images of the object in different directions. Typically, the object is stationary while a single x-ray source rotates around the object and produces the images at different rotation angles. The collection of the projected images can then be used to reconstruct a three-dimensional image of the object.

Rotation of the x-ray source puts considerable demand on the system design and can reduce the imaging speed. An electron-beam computed tomography (EBCT) system can address this problem. In typical EBCT systems, electrons produced by the cathode are scanned across the surface of the anode located in the gantry, which consists of a metal ring or multiple rings. The scanning is accomplished by electrical and magnetic fields. However, the machine is expensive and takes significantly larger space than a regular computed tomography system. Thus, it is highly desirable to have a small stationary x-ray source computed tomography system that is potentially more transportable and cost effective.

In some systems, such as tomography, the x-ray source is stationary and the object is rotated to collect the projection images. In the micro-computed tomography systems, the x-ray source typically produces a fan beam onto the object. In some cases, a cone beam and two-dimensional detector are used to record the images. The object is rotated and an image is collected at every rotation angle. An example of the two-dimensional area detector consists of a scintillation crystal that converts the x-ray photon to visible light, and a charge-coupled-detector (CCD) camera positioned behind the crystal that captures the image. Solid state and gas detectors are also commonly used.

From the point of view of image quality, it is preferred to use a monochromatic x-ray. This is because computed tomography measures, essentially, the linear absorption coefficient, which depends on the energy of the incident x-ray photon. However, in most computed tomography systems, with the exception of a synchrotron radiation source, continuous-energy x-ray rather than monochromatic x-ray is used so as to increase the x-ray intensity, and thus reduce the data collection time. In many computed tomography systems, the x-ray source is often placed far away from the object to minimize the non-even spatial distribution of the x-ray radiation from the single x-ray source and the divergence of the x-ray beam. As a result, only a small fraction of the produced x-ray photons are used for imaging.

It is highly desirable to have an all-stationary computed tomography system. Such a system will reduce or eliminate the need to rotate the x-ray source around the patient. Furthermore, novel x-ray source geometries combined with the precise control of these x-ray sources can allow the development of imaging techniques and the refinement of current data acquisition methods.

SUMMARY OF THE INVENTION

An exemplary embodiment of a computed tomography device comprises an x-ray source, and an x-ray detecting unit. The x-ray source comprises a cathode with a plurality of individually programmable electron emitting units that each emit an electron upon an application of an electric field, an anode target that emits an x-ray upon impact by the emitted electron, and a collimator.

An exemplary method to operate a computed tomography device, the computed tomography device including an x-ray source, the x-ray source comprising a cathode with a plurality of individually programmable electron emitting units that each emit an electron upon an application of an electric field, an anode target that emits an x-ray upon impact by the emitted electron, a collimator, and an x-ray detecting unit, comprises applying the electric field to at least a first of the plurality of individually programmable electron emitting units to cause the emission of an electron, focusing the emitted electron at one of a plurality of focal points on the anode target, impacting the anode target with the emitted electron to form an emitted x-ray radiation, collimating the emitted x-ray radiation, passing the collimated x-ray radiation through an object, detecting the x-ray radiation with the x-ray detecting unit, and recording the detected x-ray radiation.

BRIEF DESCRIPTION OF THE DRAWING FIGURES

Objects and advantages of the invention will become apparent from the following detailed description of preferred embodiments thereof in connection with the accompanying drawings in which like numerals designate like elements and in which.

DETAILED DESCRIPTION OF PREFERRED EMBODIMENTS

The x-ray systems and x-ray imaging methodologies for computed tomography disclosed herein are based on our previous disclosures, including U.S. patent application Ser. No. 09/679,303 entitled "X-RAY GENERATING MECHANISM USING ELECTRON FIELD EMISSION CATHODE", U.S. patent application Ser. No. 10/051,183 entitled "LARGE-AREA INDIVIDUALLY ADDRESSABLE MULTI-BEAM X-RAY SYSTEM AND METHOD OF FORMING SAME", and U.S. patent application Ser. No. 10/309,126 entitled "X-RAY GENERATING MECHANISM USING ELECTRON FIELD EMISSION CATHODE", the entire disclosures of all these applications are herein incorporated by reference. U.S. patent application Ser. No. 09/679,303 discloses an x-ray generating device incorporating a nanostructure-containing material. U.S. patent application Ser. No. 10/051,183 discloses a structure to generate x-rays having a plurality of stationary and individually electrically addressable field emissive electron sources with a substrate composed of a field emissive material, such as carbon nanotubes, that can be electrically switched at a predetermined frequency to field emits electrons in a programmable sequence.

Figure 1:
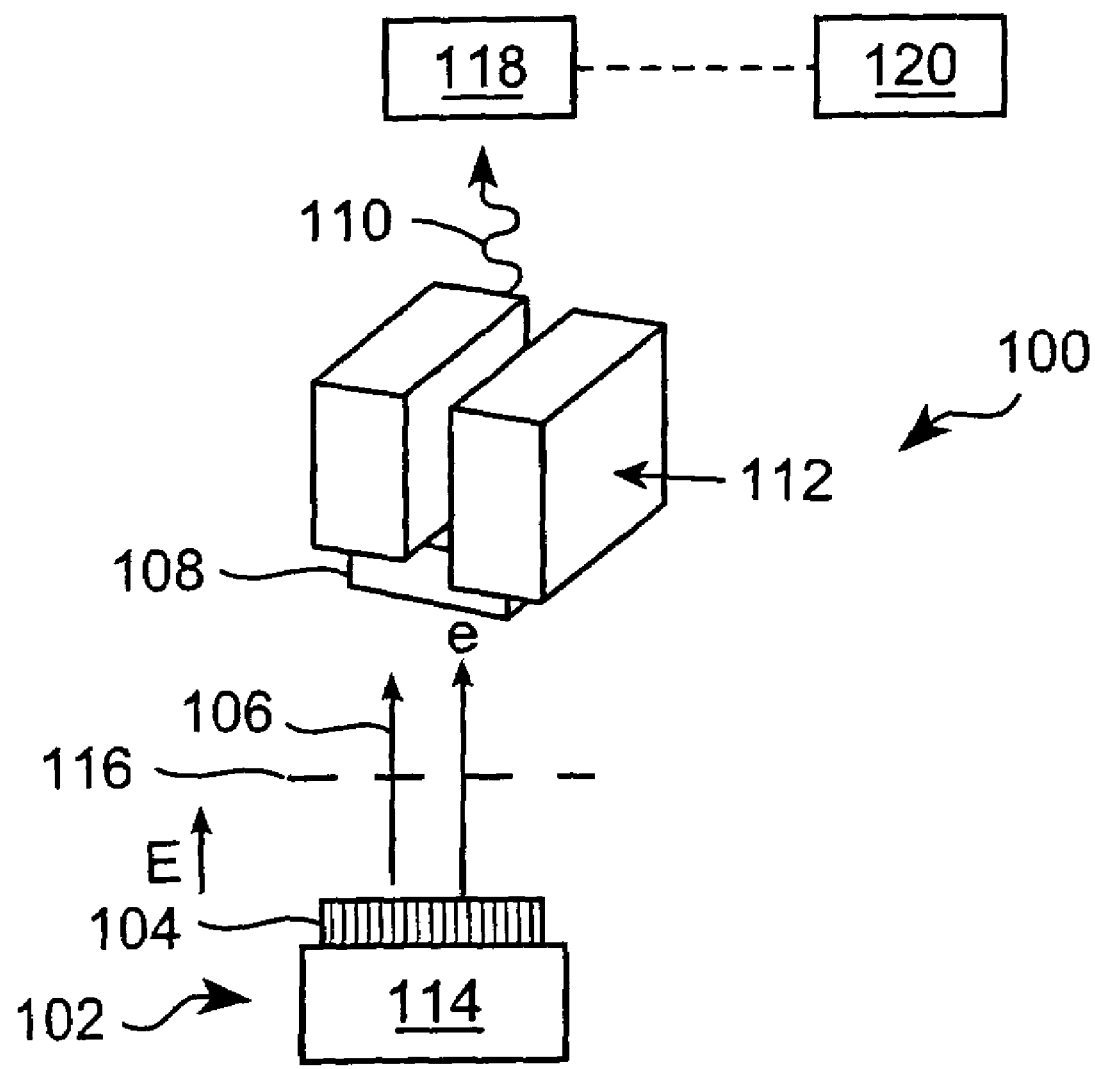
FIG. 1 shows a schematic representation of an exemplary x-ray radiation source.

An exemplary embodiment of a computed tomography device comprises an x-ray source and an x-ray detecting unit. FIG. 1 shows a schematic representation of an exemplary x-ray radiation source 100. The x-ray source 100 includes a cathode 102 with a plurality of individually programmable electron emitting units 104 that each emit an electron 106 upon an application of an electric field (E), an anode target 108 that emits an x-ray 110 upon impact by the emitted electron 106, and a collimator 112.

In exemplary embodiments, the electron emitting unit 104 includes an electron field emitting material. For example, the electron field emitting material can include a nanostructured material. In a further example, the electron field emitting material includes a plurality of nanotubes or a plurality of nanowires. The nanotubes can include inorganic materials. For example, the nanowires can include at least one field emitting material selected from the group consisting of carbon, boron, nitrogen, sulfur, and tungsten. The nanowires can included at least one field emitting material selected from the group consisting of silicon, germanium, carbon, oxygen, indium, cadmium, gallium, oxide, nitrides, silicides and boride. The nanowires can be fabricated by a variety of techniques including chemical vapor deposition, solution synthesis, and laser ablation. The paper by J. Hu, et al., "Chemistry and Physics in One Dimension: Synthesis and Properties of Nanowires and Nanotubes", Accounts of Chemical Research, Vol. 32, pages 435–445, 1999, the entire content of which is incorporated herein by reference, describes some of these fabrication methods.

The cathode 102 can include one or more individually programmable and/or addressable electron emitting units 104 arranged on a support structure 114. In an exemplary embodiment, the electron emitting unit 104 is one or more electron emitting pixels. The electron emitting pixels can be any suitable electron source. In an exemplary embodiment, the electron emitting pixels are electron field emission sources, such as electron field emitting materials including a plurality of single-wall carbon nanotubes (SWNT), a plurality of multi-wall carbon nanotubes (MWNT), a plurality of double-wall carbon nanotubes (DWNT), or a mixture thereof. Examples of suitable electron field emission sources include the carbon nanotube based electron field emission sources disclosed in U.S. patent application Ser. No. 09/296,572 entitled "DEVICE COMPRISING CARBON NANOTUBE FIELD EMITTER STRUCTURE AND PROCESS FOR FORMING DEVICE", the entire disclosure of which is incorporated herein by reference, which discloses a carbon nanotube-based electron emitter structure, U.S. patent application Ser. No. 09/351,537 entitled "DEVICE COMPRISING THIN FILM CARBON NANOTUBE ELECTRON FIELD EMITTER STRUCTURE", the entire disclosure of which is incorporated herein by reference, which discloses a carbon-nanotube field emitter structure having a high emitted current density, U.S. Pat. No. 6,277,318 to Bower et al. entitled "METHOD FOR FABRICATION OF PATTERNED CARBON NANOTUBE FILMS", the entire disclosure of which is incorporated herein by reference, which discloses a method of fabricating adherent, patterned carbon nanotube films onto a substrate, U.S. patent application Ser. No. 09/679,303 entitled "X-RAY GENERATING MECHANISM USING ELECTRON FIELD EMISSION CATHODE", the entire disclosure of which is incorporated herein by reference, which discloses an x-ray generating device incorporating a nanostructure-containing material, U.S. patent application Ser. No. 09/817,164 entitled "COATED ELECTRODE WITH ENHANCED ELECTRON EMISSION AND IGNITION CHARACTERISTICS", the entire disclosure of which is incorporated herein by reference, which discloses an electrode including a first electrode material, an adhesion-promoting layer and a carbon nanotube-containing material disposed on at least a portion of the adhesion promoting layer, as well as associated devices incorporating such an electrode, and U.S. patent application Ser. No. 09/881,684 entitled "METHOD OF MAKING NANOTUBE-BASED MATERIAL WITH ENHANCED FIELD EMISSION", the entire disclosure of which is incorporated herein by reference, which discloses a technique for introducing a foreign species into the nanotube-based material in order to improve the emission properties thereof.

Preferably the electron emitting pixels can be controlled individually, e.g., each electron emitting pixel can be individual electrically addressed and a controller can supply an electronic field to the electron emitting pixel in any desired manner, such as individually, as a group or plurality, in a specified sequence or pattern, or randomly. A suitable method of individual control is disclosed in U.S. patent application Ser. No. 10/051,183, the entire contents of which is hereby incorporated by reference. U.S. patent application Ser. No. 10/051,183 discloses individual control by electrically switching the field emissive electron sources at a predetermined frequency to field emit electrons in a programmable sequence toward an incidence point on a target and to thereby generate x-rays corresponding in frequency and in position to that of the field emissive electron source. Other suitable methods of control are disclosed in U.S. patent application Ser. No. 09/679,303 and in U.S. patent application Ser. No. 10/309,126, the entire content of each is hereby incorporated by reference. Other examples of individual control are disclosed in Brodie and C. A. Spindt, "Vacuum Microelectronics," Advances in Electronics and Electron Physics, vol. 83, p. 1–106 (1992).

The x-ray source can further comprise a gate electrode. The exemplary embodiment of an x-ray source 100 shown in FIG. 1 includes a gate electrode 116 located between the cathode 102 and the anode target 108. The gate electrode 116 can extract the emitted electron 106 from one or more of the plurality of individually programmable electron emitting units 104 when the electrical field is applied between the gate electrode 116 and the one or more individually programmable electron emitting units 104. For example, the electrical field can be applied such that the gate electrode 116 is at a positive potential with respect to the one or more of the plurality of individually programmable electron emitting units 104. The field strength of the electrical field can be from 0.1 Volt/μm (V/μm) to 100 V/μm, preferably from 0.5 V/μm to 20 V/μm. At least one of the plurality of individually programmable electron emitting units has an emission threshold of less than 3 V/μm for greater than 0.01 mA/cm$^2$ current density, preferably greater than 0.1 mA/cm$^2$ current density, and emits 0.1–100 mA total current. In an exemplary embodiment, the emission current is approximately less than or equal to 100 μA per nanotube at an electrical field of less than 100 V/μm.

Figure 2:
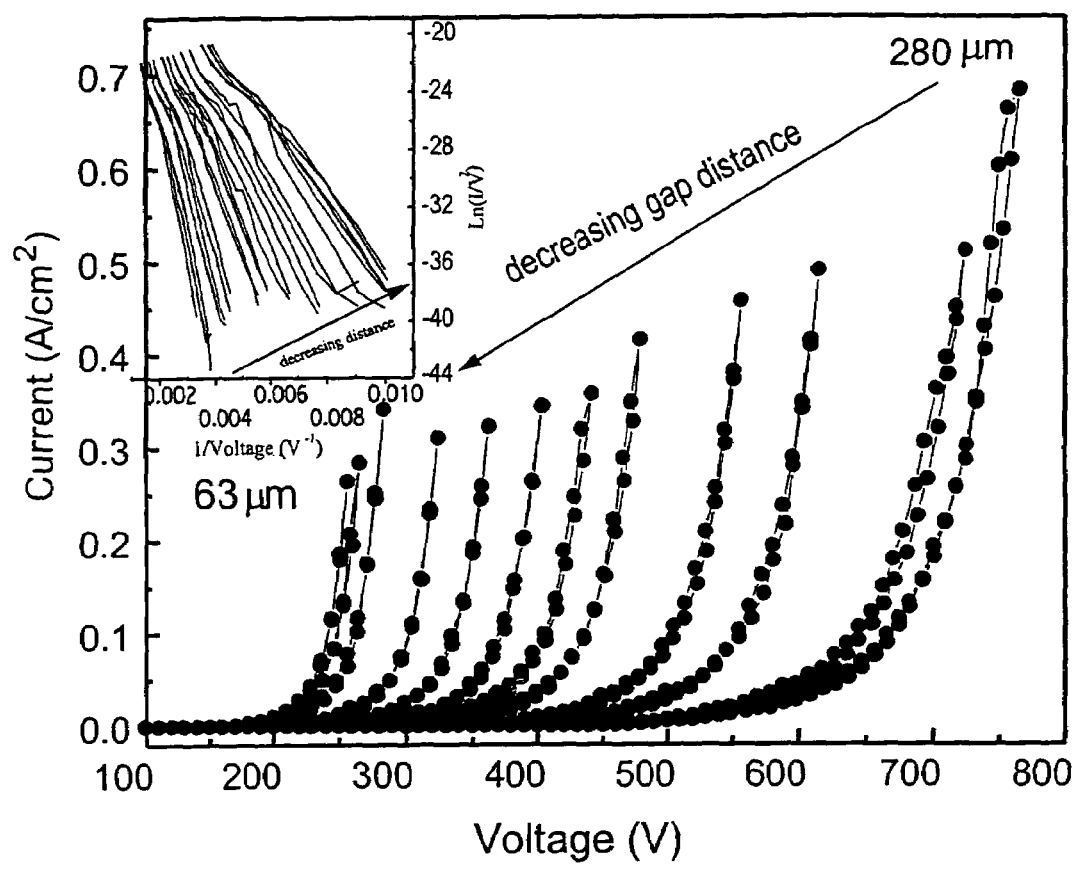
FIG. 2 shows current density as a function of voltage for carbon nanotube cathodes having a gap distance between 62 μm and 280 μm.

FIG. 2 shows current density (A/cm$^2$) as a function of voltage for carbon nanotube cathodes having a gap distance between 62 μm and 280 μm. As the gap distance decreases, the current density also decreases. Table 1 summarizes values of current density for a given electrical field. The values in FIG. 2 and Table 1 are merely examples, and values may vary significantly, depending on the sample preparation and how the measurement is performed.

TABLE 1

Emission Characteristics for the Cathode

| Current Density (mA/cm$^2$) | Electrical Field (V/μm) |
|---|---|
| 1 | 2 |
| 10 | 2.5 |
| 100 | 4 |
| 700 | 5.3 |

The emission current-voltage (I-V) characteristics of the single-wall carbon nanotube film shown in FIG. 2 and Table 1 were measured using a hemispherical current collector with a 1 millimeter (mm) diameter (anode) at 5×10$^{-8}$ Torr base pressure and different anode-cathode gap distances. As shown in the FIG. 2 and the inset to FIG. 2, the carbon nanotube film exhibits the classic Fowler-Nordheim behavior with a threshold field of 2 V/μm for 1 mA/cm$^2$ current density. The effective emission area was calculated using a previously described method as disclosed in W. Zhu, C. Bower, O. Zhou, G. P. Kochanski, and S. Jin, Appl. Phys. Lett., vol. 75, p. 873, (1999), the entire contents of which are herein incorporated by reference. The corresponding electric fields for various electron current densities are listed in Table 1. Emission current density over 1 A/cm$^2$ was readily achieved.

The emission material was purified single-wall carbon nanotube (SWNT) bundles that were produced by the laser ablation method, as disclosed in O. Zhou, H. Shimoda, B. Gao, S. J. Oh, L. Fleming, and G. Z. Yue, "Materials Science of Carbon Nanotubes: Fabrication, Integration, and Properties of Macroscopic Structures of Carbon Nanotubes", Acc. Chem. Res, vol. 35 p. 1045–1053 (2002), the entire contents of which are herein incorporated by reference. The emission material contains approximately 95-wt. % SWNT bundles with an average SWNT diameter of 1.4 nanometers (nm) and a bundle diameter of approximately 50 nm. Uniform SWNT film were coated on a flat metal disc by electrophoretic deposition, substantially similar to that disclosed in U.S. patent application Ser. No. 09/996,695, the entire contents of which are herein incorporated by reference. To increase the adhesion between the SWNT coating and the substrate, an iron inter-layer was first deposited on the substrate surface by either thermal evaporation or electrochemical plating before nanotube deposition, substantially similar to that disclosed in U.S. Pat. No. 6,277,318, the entire contents of which are herein incorporated by reference. The thickness and packing density of the nanotube film were controlled by the current, deposition time and the concentration of the nanotube suspension. The films were vacuum annealed at 800° C. before use.

An exemplary embodiment of a computed tomography device also includes an x-ray detecting unit 118. Any x-ray detecting unit can be used. For example, the x-ray detecting unit can include an x-ray scintillation material and a digital imaging acquisition device. A suitable digital imaging acquisition device includes a charge-coupled-device (CCD) or a solid state based or gaseous based imaging device. In addition, the computed tomography device can have a control system between the x-ray detecting unit and a controller, a storage device, or a combined controller/storage device 120 for data collection, storage and reconstruction. The digital imaging acquisition device digitally records the x-ray intensity of the x-ray radiation. Depending on the size and orientation of an object being imaged, e.g., an object located on an object support stage, each beam of x-ray radiation can pass through, e.g., transmission x-ray source, or can reflect from, e.g., reflection x-ray source, a portion of the object. The x-ray radiation is then detected by the corresponding x-ray detecting unit.

Figure 3:
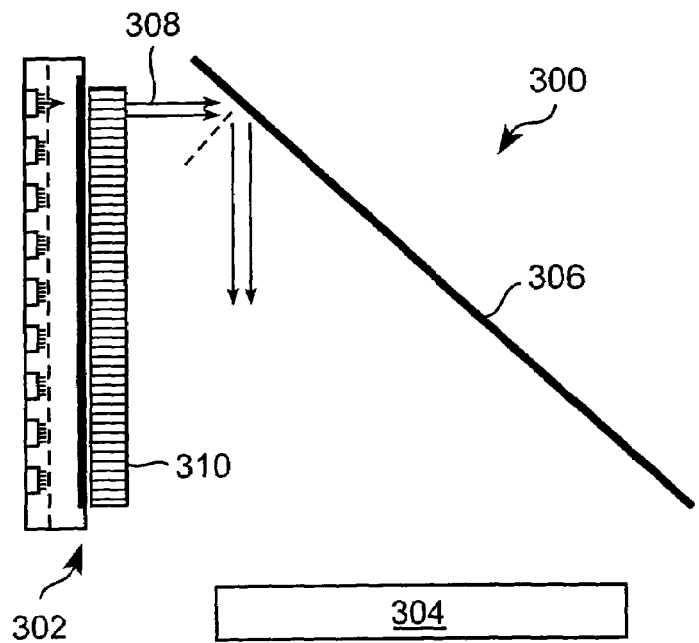
FIG. 3 shows a schematic representation of an exemplary embodiment of a collimated monochromatic x-ray radiation source.

FIG. 3 is a schematic representation of an exemplary embodiment of a collimated monochromatic x-ray radiation source 300. The collimated monochromatic x-ray radiation source 300 includes an x-ray source 302 and an x-ray detecting unit 304, both of which can be substantially similar to that described herein with respect to FIG. 1. In addition, the collimated monochromatic x-ray radiation source 300 includes a monochromator 306 placed in a path of the emitted x-ray 308 after the collimator 310. An example of a suitable monochromator includes a crystal that selects an x-ray photon with a certain energy. Examples of suitable crystals include a single crystal of graphite or silicon (Si). The energy of the outgoing x-ray beam is selected by the diffraction conditions. A particular diffraction angle is chosen to produce a diffracted beam with a predetermined energy. By choosing different diffraction angles, monochromatic x-ray beams with different energies can be selected.

An exemplary embodiment of a computed tomography system can have an x-ray source having any suitable geometry for directing a desired form of an x-ray beam toward an object of interest, such as medical applications for a patient or an animal and industrial and inspection applications such as for a structure or a container. For example, an x-ray source can be a linear, an arched, and/or an area x-ray source.

Figure 4:
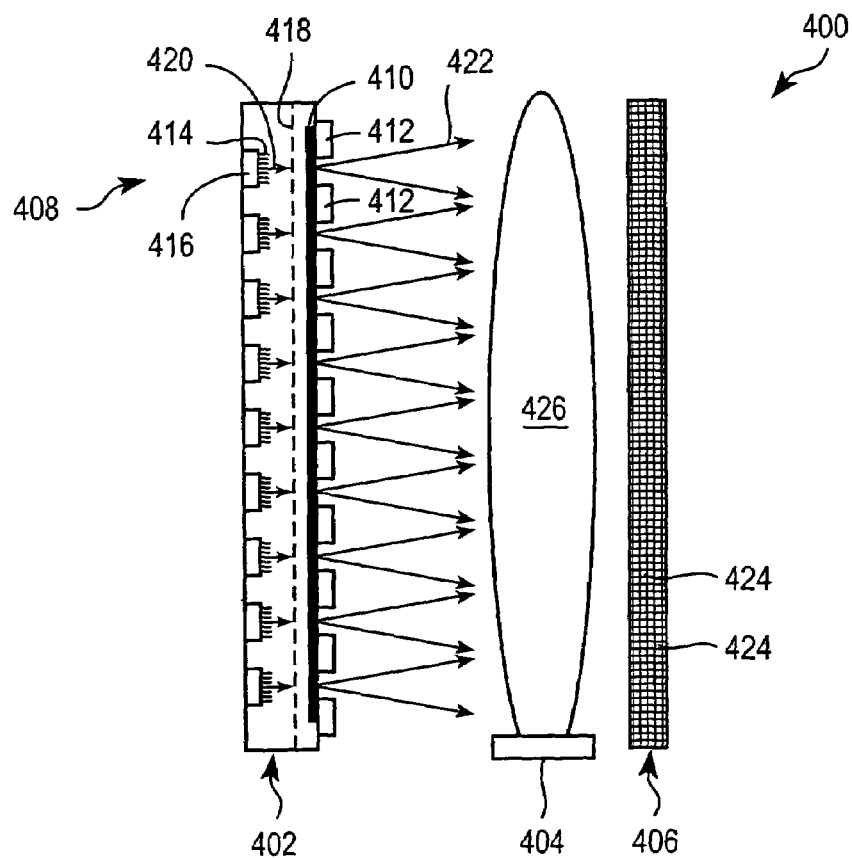
FIG. 4 shows a schematic representation of an exemplary embodiment of a linear x-ray radiation source with a fan-beam.

FIG. 4 is a schematic representation of an exemplary embodiment of a computed tomography device. The computed tomography device 400 comprises a linear scanning x-ray source 402, an object support stage 404, and a detector 406. The linear scanning x-ray source 402 comprises a cathode 408 and an anode target 410 and a collimator 412. The cathode 408 includes an array of individually programmable electron emitting units 414 arranged on a support structure 416.

A suitable arrangement of the plurality of individually programmable electron emitting units 414 includes arrangement linearly on an axis in a plane. Each individually programmable electron emitting unit is focused at one of a plurality of focal spots on the anode target 410.

The linear scanning x-ray source can have either transmission geometry or reflection geometry. In an example of a linear scanning x-ray source with a transmission geometry, the anode is a metal film which can be either free-standing or deposited on a low-atomic number material, such as carbon. The anode is at a higher electrical potential with the cathode. In one particular example, the anode is electrically grounded. A negative potential is applied to the cathode. A gate electrode, can be included in the x-ray source and can be at a positive potential with respect to the cathode to extract the electrons from the cathode.

In one particular example, all of the programmable electron emitting units are at the same potential. Each programmable electron emitting unit has a corresponding gate electrode. Electrons are extracted from a particular programmable electron emitting unit when the electrical field established between said unit and the corresponding gate exceeds a critical value (for example 3V/µm or less).

In another exemplary embodiment, the distance between the anode and the cathode is such that the electrical field due to the anode voltage is sufficient to extract the filed-emitting electrons from the cathode. In this embodiment, a reverse bias voltage is applied on the gate electrode to suppress electron emission from certain emitting units. This reverse bias voltage is scanned across the gate electrode to suppress a first group of electron filed emitting units and/or to activate a second group of programmable electron emitting units.

Each individually programmable electron emitting unit comprises a layer of electron field emitting material. Individual or groups of electron field emitting material in the layer can form an array or matrix or pattern of electron emitting pixels. In the exemplary embodiment of FIG. 4, the electron field emitting material is a layer of carbon nanotubes, but any suitable field emitting material can be used including nanostructured material and nanotubes and nanowires as substantially described herein with respect to FIGS. 1 and 3. For example, a layer of carbon nanotubes, e.g., single-walled nanotubes, multi-walled nanotubes, double-walled nanotubes, or mixtures thereof. The field emitters can also be lithographically formed Spindt-type tips.

Under an applied potential between the cathode 404 and a gate electrode 418, electrons 420 are emitted from the each of the electron emitting units 414. The field emission of electrons from the array of electron emitting units can be from a single pixel, a group of pixels, either randomly arranged or in a pattern, or all the pixels, as determined by the controlled application of the applied potential. For example, a bias potential applied between the gate and the cathode extracts electrons. A large, e.g. on the order of 10 to 200 KV/cm or greater, electrical voltage is further established between the gate and the anode to accelerate the emitted electrons to the desired energy level. The emitted electrons from the electron emitting units are accelerated and impinge on the anode target 410, for example, each at a corresponding x-ray emitting pixel. An example of an x-ray emitting pixel includes a thin layer of metal target material, such as copper (Cu) and tungsten (W), a heat dissipating target supporting material. X-ray radiation 422 is emitted from the anode when it is bombarded by the electrons, e.g., the anode is a target for the accelerated electrons. The emitted x-ray radiation passes through the collimator 412 and optionally a monochromator (not shown in FIG. 4). The collimator 412 enables each x-ray emitting pixel to generate a particular geometry of x-ray radiation 422, such as an uniform fan beam geometry. However, any suitable geometry of x-ray radiation 420 can be formed, including a pencil beam geometry or a cone beam geometry.

The computed tomography device 400 has an x-ray detector 406. An exemplary x-ray detector 406 comprises a plurality of x-ray detecting units 424. Each x-ray detecting unit 424 includes x-ray scintillation materials and a digital imaging acquisition device, such as a charge-coupled-device (CCD) or a solid state based or gaseous based imaging device. The digital imaging acquisition device digitally records the x-ray intensity of the x-ray radiation 422. Depending on the size and orientation of an object 426 on the object support stage 404, each beam of x-ray radiation 422 can pass through, e.g., transmission x-ray source, or can reflect from, e.g., reflection x-ray source, a portion of the object 426. The x-ray radiation 422 is then detected by the corresponding x-ray detecting unit 424.

In the exemplary embodiment illustrated in FIG. 4, the x-ray detector includes a two-dimensional matrix of x-ray detecting units. The detection scheme depends on the type of x-ray beams generated by the linear x-ray source. In one embodiment, an x-ray beam with fan-beam geometry is produced from each focal spot on the anode. The fan beam illuminates a slice of the object 426. The illuminated area is defined by the geometry of the collimator used. The intensity of the x-ray beam from a particular focal spot passing through the object is measured by a pre-selected set of x-ray detection units on the x-ray detector. Each focal spot is associated with a set of x-ray detection units on the x-ray detector.

To collect the images of the object, two modes can be used. In one mode, the electron emitting units are activated one by one to produce an x-ray beam from the anode that is moving through the focal spots sequentially. During scanning, the corresponding x-ray detection unit on the x-ray detector is also switched on to record the image from a particular x-ray beam, e.g., switched on sequentially or one-by-one. In another mode, all the electron emitting units are turned on at the same time. The x-ray detecting units are also switched on at the same time to collect and/or record the images of the object.

In another embodiment, the collimators are designed such that x-ray radiation with cone-beam geometry is generated from each focal spot. In this case, the electron emitting units are activated sequentially or one-by-one. When a particular unit is turned on, a cone-beam x-ray is generated from the corresponding focal spot on the anode. The x-ray beam illuminates the entire object 426. The image of the object formed by this particular x-ray beam is collected and/or recorded by the entire x-ray detector. The image is then stored in, for example, a computer. The next electron emitting unit in the sequence is then switched on to generate another image of the entire object, from a different projection angle. The process repeats for all, or a subset of all, the emitting units in the x-ray source.

Figure 5:
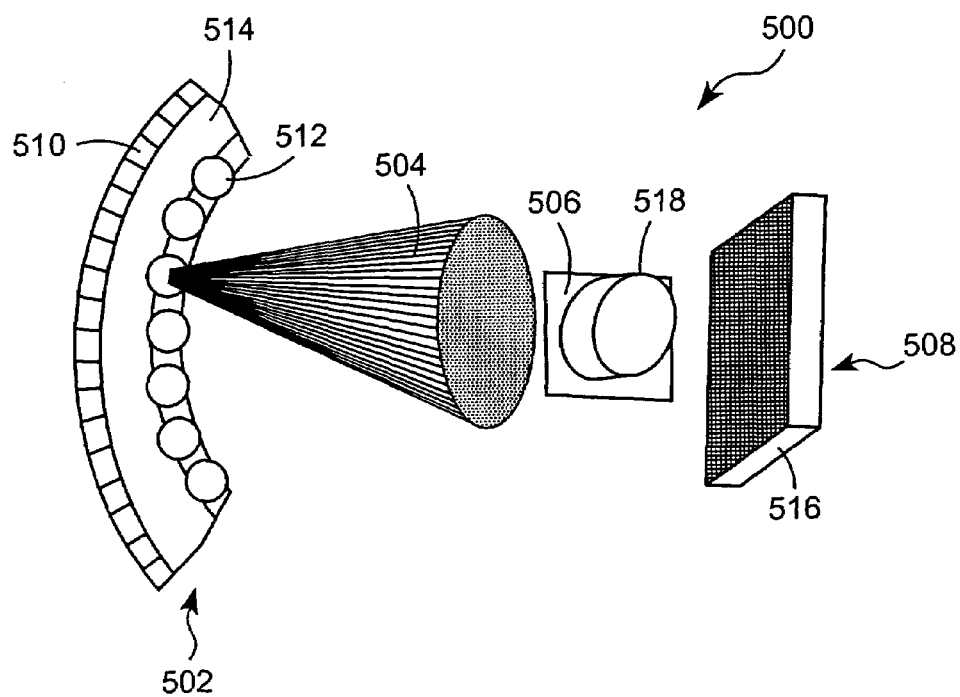
FIG. 5 shows a schematic representation of an exemplary embodiment of an arch x-ray radiation source with a cone-beam.

FIG. 5 shows a schematic representation of an exemplary embodiment of a computed tomography device 500 with a linear scanning x-ray source 502 arranged as an arch x-ray source. The x-ray source 502 generates a particular geometry of x-ray radiation 504, such as a cone beam geometry. However, any suitable geometry of x-ray radiation 504 can be formed by selection of a suitable collimator, including a pencil beam geometry or a fan beam geometry. In the exemplary embodiment shown in FIG. 5, the computed tomography device 500 includes a linear scanning x-ray source 502, an object rotation stage 506, and a detector 508. The linear scanning x-ray source 502 includes a series of cathodes 510 and corresponding anode targets 512 lining the arched-shaped support structure 514. The x-ray source 502 and x-ray detecting unit 508 can be substantially similar to that described herein with respect to the x-ray source and x-ray detecting unit of FIGS. 1 and 3.

The arched-shaped support structure 514 is constructed such that each focal spot on the anode is at an equal distance from the center of an object rotation stage, e.g., from a center of rotation of an object stage or from a central rotation axis of the object stage. Further, in a preferred case, the two-dimensional detector has a curved surface so that each detecting unit is also equidistant to the object.

The computed tomography device 500 in FIG. 5 has an x-ray detector 508. As described herein, the x-ray detecting unit can be of any suitable type and/or any suitable arrangement, based on the geometric form of the x-ray radiation generated by the x-ray source. Similar to the geometry described above, the preferred geometry of the detector surface is a curved one so that each detecting unit is equidistance to the object. An exemplary x-ray detector 508 comprises a plurality of x-ray detecting units 516. Each x-ray detecting unit 516 includes x-ray scintillation materials and a digital imaging acquisition device, such as a charge-coupled-device (CCD) or a solid state based or gaseous based imaging device. The digital imaging acquisition device digitally records the x-ray intensity of the x-ray radiation 504. Depending on the size and orientation of an object 518 on the object support stage 506, each beam of x-ray radiation 504 can pass through, e.g., transmission x-ray source, or can reflect from, e.g., reflection x-ray source, a portion of the object 518. The x-ray radiation 504 is then detected by the corresponding x-ray detecting unit 516.

Figure 6:
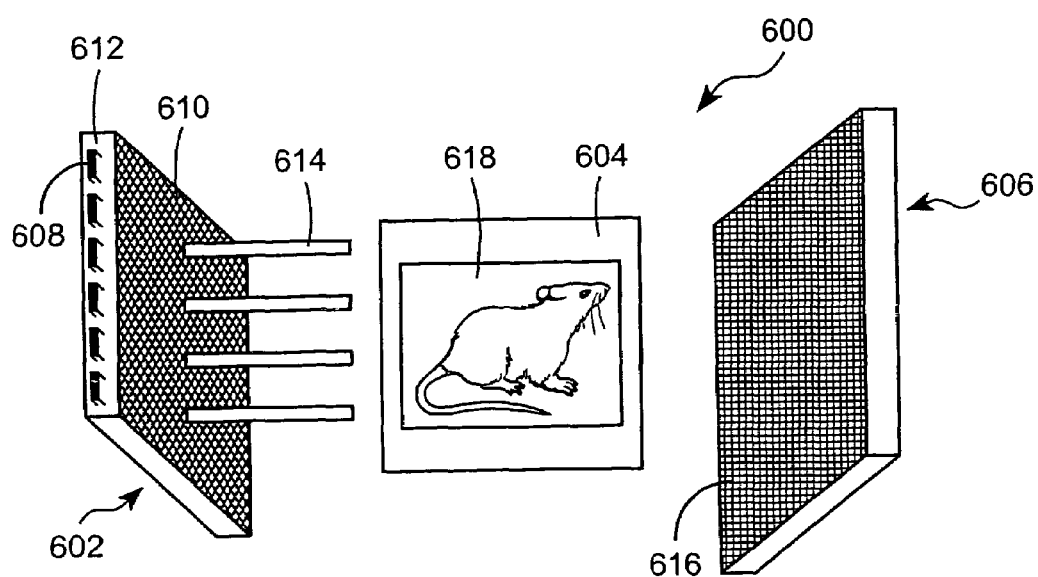
FIG. 6 shows a schematic representation of an exemplary embodiment of an area x-ray radiation source with a pencil-beam.

FIG. 6 shows a schematic representation of an exemplary embodiment of a computed tomography device 600. The computed tomography device 600 includes an area scanning x-ray source 602, an object rotation stage 604, and a detector 606. The linear scanning x-ray source 602 includes a series of cathodes 608 and corresponding anode targets 610 lining the planar-shaped support structure 612. The x-ray source 602 and x-ray detecting unit 606 can be substantially similar to that described herein with respect to FIGS. 1 and 3. The computed tomography device 600 has an area linear scanning x-ray source 602 arranged as a planar x-ray source generating a particular geometry of x-ray radiation 614, such as a pencil beam geometry. However, any suitable geometry of x-ray radiation 614 can be formed by selection of a suitable collimator, including a cone beam geometry or a fan beam geometry. In the exemplary embodiment shown in FIG. 6, The individually programmable electron emitting units of the cathode are arranged over an area of the planar-shaped support structure and each individually programmable electron emitting unit is focused at one of a plurality of focal spots on the anode target 610.

The computed tomography device 600 in FIG. 6 has an x-ray detector 606. As described herein, the x-ray detecting unit can be of any suitable type and/or any suitable arrangement, based on the geometric form of the x-ray radiation generated by the x-ray source. An exemplary x-ray detector 606 comprises a plurality of x-ray detecting units 616. Each x-ray detecting unit 616 includes x-ray scintillation materials and a digital imaging acquisition device, such as a charge-coupled-device (CCD) or a solid state based or gaseous based imaging device. The x-ray detecting units can be suitably arranged, such as in a matrix or an array. The digital imaging acquisition device digitally records the x-ray intensity of the x-ray radiation 614. Depending on the size and orientation of an object 618 on the object support stage 604, each beam of x-ray radiation 614 can pass through, e.g., transmission x-ray source, or can reflect from, e.g., reflection x-ray source, a portion of the object 618. The x-ray radiation 614 is then detected by the corresponding x-ray detecting unit 616.

A method to operate a computed tomography device includes applying an electric field to at least a first of a plurality of individually programmable electron emitting units. Applying the electric field causes the emission of an electron. The emitted electron is focused at one of a plurality of focal points on an anode target. the emitted electron impacts the anode target to form an emitted x-ray radiation, which is collimated to a geometry, such as a cone beam geometry, a pencil beam geometry, or a fan beam geometry, and passed through an object. The x-ray radiation is then detected by an x-ray detecting unit and recorded.

The method can be repeated to produce multiple detected x-ray radiation images without rotating the object positioned on the object stage. For example, each of the plurality of individually programmable electron emitting units of the x-ray source can be operated in a particular sequence or operated as a group in a particular pattern to produce an emitted x-ray that illuminates the object in the computed tomography device from a different angle, plane, or other orientation. Accordingly, by repeating the steps of applying, focusing, impacting, collimating, passing, detecting, and recording with respect to a particular sequence or grouping of individually programmable electron emitting units, multiple detected x-ray radiation images can be produced. For example, during the repetition of the operation of the computed tomography device, the electric field is applied to at least a second individually programmable electron emitting unit. Further, the emitted electrons are focused on a second of the plurality of focal points on the anode target when the step of focusing is repeated.

The step of collimating can produce an x-ray radiation beam of a particular geometry. For example, the collimator can be selected such that the emitted x-ray radiation is collimated to produce a fan beam geometry of x-ray radiation, a pencil beam geometry of x-ray radiation, or a cone beam geometry of x-ray radiation. Each of these x-ray radiation beam geometries has an associated imaging technique, such as a magnified stereo projection image, a parallel projection image, or projection images from different viewing angles for reconstruction of three-dimensional images.

During the method of operating a computed tomography device, an electric field is applied between the cathode and a gate electrode. The gate electrode is at a positive potential with respect to the individually programmable electron emitting units of the cathode. An exemplary field strength of the electric field is from 0.1 V/$\mu$m to 100 V/$\mu$m, preferably from 0.5 V/$\mu$m to 20 V/$\mu$m. The application of the electric field accelerates the emitted electrons to a given energy.

In another exemplary method, the electric field is established between the gate electrode and at least two of the plurality of individual programmable electron emitting unit sequentially. The electric field is established one individually programmable electron emitting unit or a group of individually programmable electron emitting units at a given time, from a first location on the cathode to a second location on the cathode. The applied electrical field has a predetermined frequency and pulse width. The frequency determines how many times per second the electrical field is switched on. There is a no limitation on the frequency. For example, the frequency can be in the range of 0.01–$10^6$ Hz. The pulse width determines the dwell time when the field is switched on. Again there is no limitation on the dwell time. For example, it can be in the range of one micro-second to one minute. At each sequential establishment of the electric field, a view of the object is illuminated and a x-ray image is collected. Thus, over the sequential operation, a plurality of views of the object is collected.

In another exemplary method of operating a computed tomography device, an electrical field is established between the gate electrode and at least two of the plurality of individually programmable electron emitting units. The electrical field is established sequentially, one individually programmable electron emitting unit at a given time or a group of individually programmable electron emitting units, from a first location on the cathode to a second location on cathode at a given sweep rate. For example, the sweep rate can be in the range of 0.01 Hz to $10^6$ Hz. The sequential establishment of the electrical field illuminates the object and produces a plurality of views that are subsequently collected for later retrieval and/or analysis.

In one particular embodiment of this invention, the frequency and pulse width of the electrical field applied to the gate electrode is synchronized with the data collection time of the x-ray detector. The x-ray radiation is generated only when the x-ray detector is collecting data. Synchronization of x-ray generation and data collection can significantly reduce the amount of unnecessary radiation dosage the object receives during imaging.

In yet another embodiment of the invention, the frequency and the pulse width of the electrical field applied to the gate electrode and thus the frequency and the pulse width of the x-ray produced are synchronized with either a physiological signal, an internal signal from the object, or an external signal source. For example, the frequency and the pulse width of the x-ray generated can be gated by the cardiac or respiratory signals to obtain clear images of moving object.

For a given object orientation, an x-ray radiation having a cone beam geometry originates from different focal points impinging on the object from different angles. The corresponding two-dimensional projection images are different. This is because the x-ray beams originate from different points in space and have different projection angles. As a result, by collecting a large number of images from a wide viewing angle range, internal structure of the object can be obtained. Thus, in one sweep over the linear x-ray sources, multiple two-dimensional images are acquired in short time without rotating the object. This greatly increases the image acquisition speed.

To produce a scanning x-ray beam, a pulsed electrical field between the gate and the cathode is swept through the emitting pixels at a given speed. The field is set at a value such that each pixel will emit a certain current for a given duration and in a given sequence, which is determined by the pulse width of the sweeping field. During this process, the voltage between the anode and the gate remains at a constant value. When the electrons impinge on the anode, x-ray radiation emits from the point of impact. As the electrical field sweeps through the cathode, the origin of the x-ray radiation sweeps through the surface of the anode.

The pulse-width, frequency and sweep rate of the electrical field on the gate are synchronized with the electronics that control the detector such that the images collected are in registry with the positions of the focal points. For example, a controller can synchronize the electric field and the detector.

During operation of an exemplary computed tomography device, the x-ray radiation from the x-ray source illuminates an object which is supported on the object support stage. The object support stage of an exemplary computed tomography device can be either stationary or can be rotated through a pre-determined set of angles. One example of a computed tomography system using a single beam x-ray source and a rotating sample stage is contained in M. D. Bentley, M. C. Ortiz, E. L. Ritman, and J. C. Romero, "The Use of Microcomputed Tomography to Study Microvasculature in Small Rodents," AJP Regulatory Integrative Comp Physiol, 282, R1267–R1279 (2002), the entire content of which is incorporated herein by reference.

In another method to operate a computed tomography, the object is positioned on an object stage and is rotated through a set of angles. After each rotation of the object, the steps of applying, focusing, impacting, collimating, passing, detecting, and recording are repeated to obtain a series of detected x-ray radiation images. The x-ray radiation images can then be reconstructed to form a three-dimensional volume of the object. For example, the detected x-ray radiation images can be reconstructed using an image reconstruction algorithm to form the three-dimensional volume of the object. For example, the cone-beam reconstruction algorithm developed by Feldkamp, et al. in L. A. Feldkamp, L. C. Davis, and J. W. Kress, "Practical cone-beam algorithm", J. Opt. Soc.

Am., vol. 1, 612–619 (1984), the entire content of which is herein incorporated by reference can be modified for such purpose.

The exemplary computed tomography system operates in two different modes. In a first mode, e.g., the computed tomography mode, the source and detector are rotated about the object, generating a set of three-dimensional cone beam projections for reconstruction into an image. In a second mode, a series of two-dimensional images are acquired from a single projection, resembling a fluoroscopy unit. As the two-dimensional projection direction is known, it may be mapped into the three-dimensional projection from the first mode, allowing localization of objections. Multiple array source elements may be utilized to spatially localize objects of interest.

For example, the object support stage is set to a first angle and all cathodes of the x-ray source are turned on simultaneously to generate a linear set of x-ray radiation beams. Each x-ray detecting unit records an image, such as a projection image of a slice of the object. All images are combined digitally, to form a two-dimensional image of the object for the given angle of the x-ray source. Thus, all slice projections are combined. The object support stage is then set to a second angle and the process of acquiring an image repeated. By rotating the stage, a plurality of two-dimensional images (such as 360 images, one each for 1 degree rotation of the sample) of a sample are obtained. The images can be combined in real time, or can be electronically stored for later combination.

To obtain a set of three-dimensional images of the object, the object is rotated through a set of angles, such as 30, 60, or 90 degrees. A new set of images are taken after each rotation. Only a few rotations are needed to obtain the sets of images needed to reconstruct the three-dimensional volume of the objects. The radial resolution may also be increased by rotating the object by smaller angles, such as 5, 10, or 15 degrees.

The x-ray source and detector are rotated about the object stage, which is stationary and on which a object is mounted. Image acquisition may be performed in a continuous manner with the x-ray source continuously rotating about the object. Finer radial resolution may be achieved by performing multiple acquisitions at each rotational angle with or without selectively pulsing each x-ray source.

Multiple exemplary embodiments of a computed tomography device are possible. These exemplary embodiments incorporate some or all of the features previously discussed herein.

Figure 7:
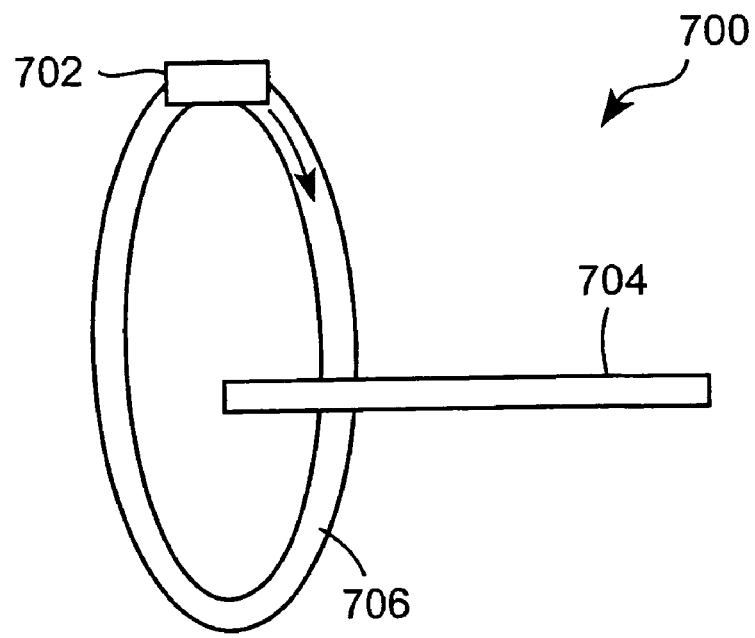
FIG. 7 shows a schematic representation of an exemplary embodiment of a CT system with a linear x-ray radiation source rotated about a stationary stage.

An exemplary embodiment of a computed tomography device is shown in FIG. 7. The computed tomography device 700 comprises a circular x-ray source 702, an object stage 704, and a circular detector 706. The circular x-ray source includes an array of x-ray producing elements facing the center of a source circle. The detectors are in a similar arrangement, e.g., in a detector circle, positioned adjacent the source circle. By controlling each of the circular x-ray sources individually, multiple slice projections can be produced without rotation of the detectors or x-ray source or with only a slight rotation e.g., 15 degrees or less. The slight rotation may be incorporated into either the source or the detectors to provide increased radial resolution. In this embodiment, near instantaneous single slice imaging can occur limited only by the switching rate of the x-ray source, which can be 106 Hz or higher, and the time necessary to acquire a projection, which depends on the sensitivity of the detector and the x-ray flux produced pulse but can be as short as a micro-second. In contrast, current medical computed tomography setups can require at least 250 to 500 msec to acquire a single slice.

Figure 8:
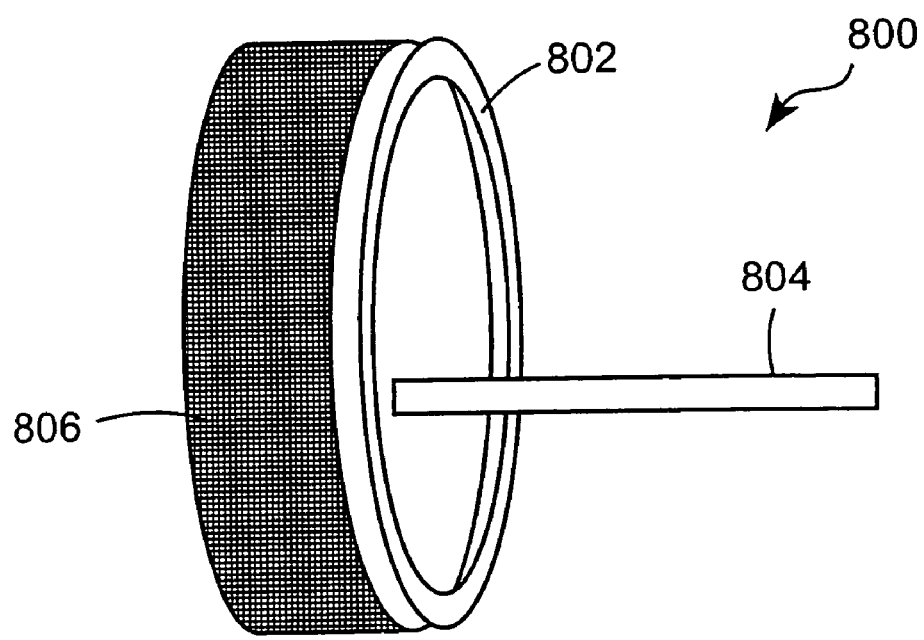
FIG. 8 shows a schematic representation of an exemplary embodiment of a CT system with a circular x-ray radiation source positioned about a stationary stage.

Another exemplary embodiment of a computed tomography device is shown in FIG. 8. The computed tomography device 800 comprises an electron beam source 802, an object stage 804, an area detector 806. The circular x-ray source consists of an array of the x-ray producing elements facing the center of a circle. The detectors are in a similar arrangement positioned adjacent the source circle. By controlling each of the x-ray sources individually, multiple slice projections may be produced, requiring no rotation of the detectors or x-ray source. A slight (15 degrees or less) rotation may be incorporated into either the source or the detectors to provide increased radial resolution. This setup allows near instantaneous single slice imaging, limited only by the switching rate of the x-ray source and the time necessary to acquire a projection. The current medical CT setups require at least 250 to 500 msec to acquire a single slice.

Figure 9:
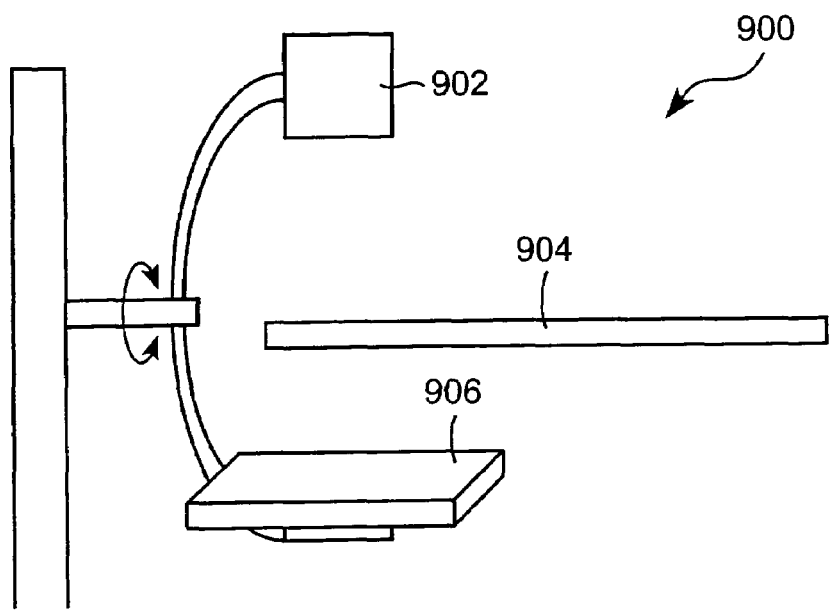
FIG. 9 shows a schematic representation of an exemplary embodiment of an x-ray radiation source that can be operated in a computed tomography mode and a single projection mode

Another exemplary embodiment of a computed tomography device is shown in FIG. 9. The computed tomography device 900 comprises an electron beam source 902, an object stage 904, an area detector 906. The system is designed to operate in two different modes. First, is the computed tomography mode, where the source and detector are rotated about the object, generating a set of 3-D cone beam projections for reconstruction. The second mode, the system acquires a series of 2-D images from a single projection, resembling a fluoroscopy unit. As the 2-D projection direction is known, it may be mapped into the 3-D projection that was measured first, allowing localization of objections. Multiple array source elements may be utilized to spatially localize objects of interest.

Figure 10:
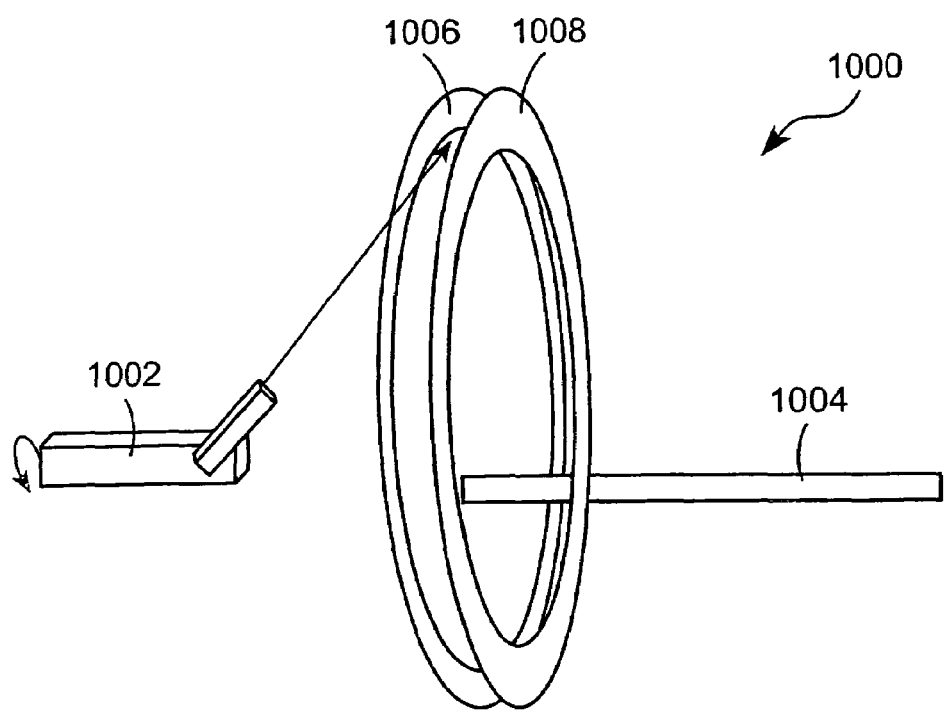
FIG. 10 shows a schematic representation of an exemplary embodiment of a CT system with a ring target, the electron beam strikes the target by reorienting the electron beam source and/or by steering the electron beam.

Another exemplary embodiment of a computed tomography device is shown in FIG. 10. The computed tomography device 1000 comprises an electron beam source 1002, an object stage 1004, an area detector 1006 and a stationary tungsten ring 1008. The source of electrons, e.g., a field emission cathode, may be physically pointed or magnetically steered at the stationary tungsten ring that surrounds the object stage. Electrons from the electron source strike the stationary tungsten ring and generate x-ray photons that are directed back at the object. Multiple projections of the x-ray may be realized by mechanically moving the electron source such that the electron beam is directed to different locations of the stationary x-ray target ring, e.g., the tungsten ring. The object remains stationary, as does the detector. A high voltage is applied between the cathode and the target ring to accelerate the electrons to the desired energy.

In exemplary embodiments, imaging techniques associated with computed tomography acquisition can be used. However, additional imaging techniques are available through the exemplary embodiments of a computed tomography device described herein. For example, traditional medical computed tomography techniques have required that the x-ray computed tomography tube be turned on in a continuous manner when circling around the patient. However, the nanotube based x-ray source allows tight switching control of the x-ray source, enabling more sophisticated imaging patterns. For example, instead of the traditional circular path of the imaging x-ray source, a star shaped pattern may be utilized, sequentially activating sources on opposite sides of the ring. Furthermore, the ability to provide short bursts of x-rays may also reduce exposure time to the object; bursts are only needed when the source and detector are positioned at the next angle—the intermediary position does not need the x-ray to be on. Any reduction of dose is of great advantage for the patient. Dose reduction may also be performed at a loss of spatial resolution; by sampling a smaller number of angles. Reducing the angular sampling may be useful in creating a rapid computed tomography screening tool. Rapid, multi-angle computed tomography fluoroscopy also becomes possible, incorporating the time resolution of a normal fluoroscopy machine, with the three-dimensional acquisition capability of the computed tomography. Tight control of the x-ray source allows prospective cardiac gating, essential in improving the image quality associated with cardiac imaging. Furthermore, an addressable x-ray source allows control of the thickness of the imaging slice at the x-ray source.

Example applications for the exemplary computed tomography devices and methods described herein can include, although not limited to, the following:

Clinical imaging: Clinical imaging applications, such as rapid full body or body part specific imaging, portable imaging units for specific body parts, such as the head for in-field diagnosis of trauma, stroke, and so forth, dynamic contrast studies for perfusion of brain, liver and other organs, gated imaging for moving body parts (lungs, heart, etc.), low dose imaging techniques for screening or pediatric purposes, fluoroscopy and diffraction imaging techniques.

Small animal imaging: Small animal imaging applications, such as small animal computed tomography for observing anatomical structure, rapid screening for identifying animal phenotype, dynamic studies in small animals (with or without contrast agents).

Industrial applications: Industrial applications, such as non-destructive testing and container inspections, e.g., customs inspections.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A method to operate a computed tomography device, the computed tomography device including an x-ray source, the x-ray source comprising a cathode with a plurality of individually programmable electron emitting units that each emit an electron beam upon an application of an electric field, an anode target that emits an x-ray beam upon impact by the emitted electron beam, a collimator, and an x-ray detecting unit, the method comprising:

applying the electric field to at least a first of the plurality of individually programmable electron emitting units to cause the emission of an electron beam;

focusing the emitted electron beam at one of a plurality of focal points on the anode target;

impacting the anode target with the emitted electron beam to form an emitted x-ray radiation beam;

collimating the emitted x-ray radiation beam;

passing the collimated x-ray radiation beam through an object;

detecting the x-ray radiation beam with the x-ray detecting unit; and recording the detected x-ray radiation beam as an x-ray radiation image, wherein the object is on an object stage and the method further comprises:

rotating the object on the object stage through a set of angles; and repeating, after each rotation of the object, the steps of applying, focusing, impacting, collimating, passing, detecting, and recording to obtain a series of x-ray radiation images.

2. The method of claim 1, comprising reconstructing a three-dimensional volume of the object positioned on the object stage from the series of x-ray radiation images.

3. The method of claim 2, wherein the x-ray radiation images are reconstructed using an image reconstructing algorithm to form the three-dimensional volume of the object.

4. A method to operate a computed tomography device, the computed tomography device including an x-ray source, the x-ray source comprising a cathode with a plurality of individually programmable electron emitting units that each emit an electron beam upon an application of an electric field, an anode target that emits an x-ray beam upon impact by the emitted electron beam, a collimator, and an x-ray detecting unit, the method comprising:

applying the electric field to at least a first of the plurality of individually programmable electron emitting units to cause the emission of an electron beam;

focusing the emitted electron beam at one of a plurality of focal points on the anode target;

impacting the anode target with the emitted electron beam to form an emitted x-ray radiation beam;

collimating the emitted x-ray radiation beam;

passing the collimated x-ray radiation beam through an object;

detecting the x-ray radiation beam with the x-ray detecting unit; and recording the detected x-ray radiation beam as an x-ray radiation image, further comprising rotating the object from a first position to a second position by an angle between 0.1 and 10 degree in a discrete step and obtaining one two-dimensional image at the first position and the second position.

5. The method of claim 4, wherein the obtained two-dimension images are combined using an image reconstruction algorithm to form a three-dimension image of the object.

6. A method to operate a computed tomography device, the computed tomography device including an x-ray source, the x-ray source comprising a cathode with a plurality of individually programmable electron emitting units that each emit an electron beam upon an application of an electric field, an anode target that emits an x-ray beam upon impact by the emitted electron beam, a collimator, and an x-ray detecting unit, the method comprising:

applying the electric field to at least a first of the plurality of individually programmable electron emitting units to cause the emission of an electron beam;

focusing the emitted electron beam at one of a plurality of focal points on the anode target;

impacting the anode target with the emitted electron beam to form an emitted x-ray radiation beam;

collimating the emitted x-ray radiation beam;

passing the collimated x-ray radiation beam through an object;

detecting the x-ray radiation beam with the x-ray detecting unit; and recording the detected x-ray radiation beam as an x-ray radiation image, wherein an electrical field is established between the gate electrode and at least two of the plurality of individually programmable electron emitting units sequentially, one individually programmable electron emitting unit at a given time, from a first location on the cathode to a second location on the cathode, the sequential establishment of the electrical field having an on-off frequency between any two sequential individually programmable electron emitting units of from 0.01 to $10^6$ Hz.

7. The method of claim 6, wherein a dwell time on each unit is from 1 μsec to 1 minute.

8. The method of claim 6, wherein a plurality of views of the object are collected.

9. A method to operate a computed tomography device, the computed tomography device including an x-ray source, the x-ray source comprising a cathode with a plurality of individually programmable electron emitting units that each emit an electron beam upon an application of an electric field, an anode target that emits an x-ray beam upon impact by the emitted electron beam, a collimator, and an x-ray detecting unit, the method comprising:

applying the electric field to at least a first of the plurality of individually programmable electron emitting units to cause the emission of an electron beam;

focusing the emitted electron beam at one of a plurality of focal points on the anode target;

impacting the anode target with the emitted electron beam to form an emitted x-ray radiation beam;

collimating the emitted x-ray radiation beam;

passing the collimated x-ray radiation beam through an object;

detecting the x-ray radiation beam with the x-ray detecting unit; and recording the detected x-ray radiation beam as an x-ray radiation image, wherein an electrical field is established between the gate electrode and at least two of the plurality of individually programmable electron emitting units sequentially, one individually programmable electron emitting unit at a given time, from a first location on the cathode to a second location on the cathode at a sweep rate of 0.01 to $10^6$ Hz.

10. The method of claim 9, wherein a plurality of views of the object are collected.

11. A method to operate a computed tomography device, the computed tomography device including an x-ray source, the x-ray source comprising a cathode with a plurality of individually programmable electron emitting units that each emit an electron beam upon an application of an electric field, an anode target that emits an x-ray beam upon impact by the emitted electron beam, and an x-ray detecting unit, the method comprising:

applying the electric field to at least a first of the plurality of individually programmable electron emitting units to cause the emission of an electron beam;

focusing the emitted electron beam at one of a plurality of focal points on the anode target;

impacting the anode target with the emitted electron beam to form an emitted x-ray radiation beam;

passing the x-ray radiation beam through an object;

detecting the x-ray radiation beam with the x-ray detecting unit, and rotating the detector and x-ray source pair from a first position to a second position by an angle between 0.1 and 10 degree in a discrete step and obtaining one two-dimensional image at the first position and the second position.

12. The method of claim 11, wherein the obtained two-dimension images are combined using an image reconstruction algorithm to form a three-dimension image of the object.

\* \* \* \* \*